(12) United States Patent
Levine

(10) Patent No.: US 9,408,935 B2
(45) Date of Patent: Aug. 9, 2016

(54) FORMULATION AND METHOD OF MAKING VITAMIN INFUSED AIR SPRAY

(71) Applicant: Kittrich Corporation, La Mirada, CA (US)

(72) Inventor: Robin K. Levine, Pasadena, CA (US)

(73) Assignee: KITTRICH CORPORATION, Pomona, CA (US)

( * ) Notice: Subject to any disclaimer, the term of this patent is extended or adjusted under 35 U.S.C. 154(b) by 97 days.

(21) Appl. No.: 14/202,231

(22) Filed: Mar. 10, 2014

(65) Prior Publication Data

US 2015/0252291 A1 Sep. 10, 2015

(51) Int. Cl.
*C11B 9/00* (2006.01)
*A61L 9/013* (2006.01)

(52) U.S. Cl.
CPC ...................................... *A61L 9/013* (2013.01)

(58) Field of Classification Search
CPC .................................... C11B 9/00; A61L 9/13
USPC ............................................................ 512/2
See application file for complete search history.

(56) References Cited

U.S. PATENT DOCUMENTS

| 4,851,212 A | 7/1989 | Winston et al. |
| 6,060,045 A * | 5/2000 | Mettler ..................... A61L 9/01 424/65 |
| 2011/0274643 A1 * | 11/2011 | Yontz ....................... A61K 8/25 424/76.1 |
| 2013/0126634 A1 | 5/2013 | Blattner et al. |

OTHER PUBLICATIONS

Dweck, Anthony C., "Natural Preservatives", SOFW Journal, Jul. 1995, pp. 1-33.
Cohen, Alison et al., "Clearing the Air: Hidden Hazards of Air Fresheners," Natural Resources Defense Council, Sep. 2007, (16 pages).
eco-me.com/store/air-freshener-vanilla, printed Feb. 17, 2014 (1 page).
eco-me.com/store/air-freshener-mint, printed Feb. 17, 2014 (1 page).
eco-me.com/store/air-freshener-berry, printed Feb. 17, 2014 (1 page).
eco-me.com/store/air-freshener-citrus, printed Feb. 17, 2014 (1 page).
facebook.com/EcoMeNaturalProducts, posted Mar. 10, 2013 (1 page).
en.wikipedia.org/wiki/Air_freshner, printed Aug. 22, 2014, pp. 1-5.
Lanier, Jennifer, "Air Freshener Health Risks," eHow, ehow.com/list_6062139_air-freshener-health-risks.html, printed Aug. 22, 2014 (2 pages).
Erickson, Kim, "Home Aroma: Healthy, All-Natural Air Fresheners," Mother Earth Living, motherearthliving.com/Green-Homes/home-aroma-healthy-all-natural-air-fresheners.aspx; Jul./Aug. 2010 (4 pages).

* cited by examiner

*Primary Examiner* — Ling Choi
*Assistant Examiner* — Lanee Reuther
(74) *Attorney, Agent, or Firm* — Leason Ellis LLP

(57) ABSTRACT

A formulation for a 100% natural non-aerosol air freshener infused with vitamins. The formulation may further include plant material known to have naturally occurring fungicidal, bactericidal, disinfectant, germicidal, antiseptic, antibiotic and/or antimicrobial properties. Also, a method of preparing a formulation for a 100% natural non-aerosol air freshener infused with vitamins.

22 Claims, No Drawings

FORMULATION AND METHOD OF MAKING VITAMIN INFUSED AIR SPRAY

FIELD OF THE INVENTION

The present invention pertains generally to non-aerosol air fresheners. More particularly, the present invention pertains to safe and natural non-aerosol air fresheners infused with vitamins.

BACKGROUND OF THE ART

Our sense of smell is a powerful tool used to judge a location's healthfulness and cleanliness, which is why retailers offer such a wide array of chemical sprays, gels, solids and plug-ins to scent our spaces. Three-quarters of all American homes are now scented with some type of commercial air freshener, an increase of nearly 30 percent since 1999.

Synthetic scents contain harmful chemicals. A study published in the Archives of Environmental Health linked chronic exposure to the volatile organic compounds (VOCs) in air fresheners to headaches and depression in new mothers and diarrhea and ear aches in their babies.

Harmful VOCs in air fresheners include benzene and formaldehyde, which are byproducts of the manufacturing process. Benzene exposure can damage bone marrow, which can decrease red blood cells and affect immunity. Long-term exposure to airborne benzene has also been linked to increased risk of anemia and leukemia. Formaldehyde, a known carcinogenic neurotoxin, can irritate the eyes, nose, throat and skin.

Most air fresheners—even some labeled "all natural"—use phthalates as fixatives. Easily inhaled or absorbed through the skin, these chemicals accumulate in the body's fatty tissue and liver, where they can remain for decades. High phthalate levels have been shown to cause low sperm counts and reproductive damage to male rat fetuses.

There are two broad air freshener categories: continuous action and instant action. Continuous action products include: scented candles and devices which use a candle flame or some other heat source to heat and vaporize a fragrance formulation, Incense burners, wall plug-ins which either use piezoelectric technology to aerosolize fragrance or heat to vaporize it, fragrance impregnated gels which release fragrance as the gel evaporates sometimes with the help of an electric fan, wick and reed diffusers which release fragrance by evaporation from fragrance-soaked wicks or wooden reeds; and fragrance impregnated materials like floor wax, paper, plastics, wood which release fragrance by off gassing; and lastly nebulization systems which convert liquid fragrances into a vapor in a cold process without the use of heat.

Instant action systems are mainly aerosol sprays, or atomizers. The aerosol spray uses a propellant and fragrance packaged under pressure in a sealed metal or glass container with a valve which is opened by pressing down a button which contains a spray nozzle—the actuator. When the container's valve is opened by pressing the actuator, fragrance is forced through the spray nozzle located inside the actuator to create a mist of droplets containing fragrance. These droplets are 30 to 50 micrometers in diameter. The atomizer is a glass, metal or plastic container of fragrance which operates in a similar fashion except that the actuator is a pump which when pressed a few times creates the pressure to aspirate the fragrance from the container through a tube into the actuator and spray nozzle. The mist created contains droplets 50 to 150 micrometers in diameter.

Many aerosol air fresheners contain para-dichlorobenzene, naphthalene and formaldehyde—central nervous system depressants. Formaldehyde can cause symptoms such as headaches, ear infections, sinus problems, watery eyes, asthma, bronchitis, joint pains, chronic fatigue syndrome, dizziness and chest pain. According to the Environmental Protection Agency, formaldehyde is known to cause cancer in animals and may cause cancer in humans. Another common air freshener ingredient, P-dichlorobenzene, has been found to diminish the sense of smell and may cause cancer. Trichloroethylene, also commonly found in aerosol air fresheners, has been found to cause dizziness and irregular breathing.

According to the Natural Resources Defense Council (NRDC), a recent study found harmful chemicals known as phthalates in 12 air freshener products, including some marketed as "all-natural" and "unscented." None of the air fresheners listed phthalates on their labels. When air freshener is sprayed, the phthalates are released into the air where they can be inhaled or absorbed through a person's skin. Once in the bloodstream, they can alter hormone levels and cause other health problems. According to the State of California, five types of phthalates, including one commonly found in air fresheners, are known to cause birth defects and reproductive harm. Phthalate exposure in indoor environments has also been associated with allergic symptoms and asthma.

Non-spray air fresheners, such as those designed to plug into an outlet or stick to a hard surface have also been found to carry health risks. Many of these products contain a toxic chemical known as benzyl acetate. According to International Programme on Chemical Safety, short-term exposure to benzyl acetate can cause irritation to the eyes and respiratory tract, and it may affect the central nervous system. Benzyl acetate can be absorbed by inhalation or ingestion. Long-term repeated exposure may cause kidney damage.

There remains a need for a 100% all natural, safe and effective composition of air freshener.

In light of the above, it is an object of the present invention to provide the desired features described herein as well as additional advantages of providing an 100% natural air freshener that is infused with vitamins.

SUMMARY OF THE INVENTION

In general, the present invention is a 100% natural air freshener, comprising:

water;

vegetable glycerin;

a plant-based solubilizer;

at least one plant essential oil;

at least one natural preservative; and at least one vitamin.

The present invention also includes a method of preparing a formulation according to the present invention, wherein the method comprises:

a) filling a clean vessel with water;

b) mixing and blending at least a first preservative with the water in step a);

c) mixing and blending at least a second preservative with the solution of step b);

d) mixing a vegetable glycerin and at least one vitamin in a separate container;

e) adding the vitamin mixture with the solution of step b) at high speed;

f) mixing and blending at least one plant-based solubilizer with the solution of step e) at low speed to avoid foaming; and g) mixing and blending at least one plant essential oil with the solution of step f) at low speed to avoid foaming.

DETAILED DESCRIPTION OF THE INVENTION

Vitamins are naturally found in plants and animals. Vitamins are essential to growth, energy production, and normal nerve function. There are two different types of vitamins used by the body to support health: fat-soluble (oils) and water-soluble. Many daily recommended vitamins are commercially available in liquid form, including vitamins A, B, B complex, B1, B12, B15, B2, B5, B6, C, D, E and K.

Naturally occurring fragrant molecules include "essential" oils derived from plants. Essential oils are concentrated, hydrophobic liquids containing volatile fragrant molecules from plants. Essential oils are also known as volatile, ethereal oils or aetherolea or simply as the "oil of" the plant from which they were extracted, such as, for example, oil of clove. Oil is "essential" in the sense that it carries a distinctive scent, or essence, of the plant. Essential oils do not have any specific chemical properties in common, beyond conveying characteristic fragrances. Some essential oils such as lavender, peppermint, and *eucalyptus*, are steam distilled. Raw plant material, comprising flowers, leaves, wood, bark, roots, seeds, or peel, are put into a distillation apparatus over water. As the water is heated the steam passes through the plant material, vaporizing the volatile compounds. The vapors flow through a coil where they condense back to liquid, which is then collected in the receiving vessel.

Essential oils are derived from berries, allspice, juniper, seeds, almond, anise, celery, *cumin*, nutmeg oil, bark, *cassia*, cinnamon, *sassafras*, wood, camphor, cedar, rosewood, sandalwood, agar wood, rhizome, galangal, ginger, leaves, basil, bay leaf, common sage, *eucalyptus*, lemon grass, *melaleuca*, oregano, patchouli, peppermint, pine, rosemary, spearmint, tea tree, thyme, wintergreen, resin, frankincense, myrrh, flowers, *cannabis*, chamomile, clary sage, clove, scented *geranium*, hops, hyssop, jasmine, lavender, manuka, marjoram, rose, ylang-ylang, peel, bergamot, grapefruit, lemon, lime, orange, tangerine, root, valerian, mango, or the like, or a combination comprising at least one of the foregoing.

Examples of fragrant compounds include, for example, acai oil, almond oil, *aloe vera* oil, andiroba oil, annatto oil, babassu oil, borage oil, brazil nut oil, burit oil, camelina oil, coffee oil, copaiba oil, passion fruit oil, castor oil, coconut oil, grape seed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, *cannabis* oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, *cumin* oil, cypress, cypriol, curry leaf, davana oil, dill oil, elecampane, *eucalyptus* oil, fennel seed oil, fenugreek oil, fir, frankincense oil, galangal, *geranium* oil, ginger oil, goldenrod, grapefruit oil, grape seed oil, henna oil, helichrysum, horseradish oil, hyssop, Idaho tansy, jasmine oil, juniper berry oil, lavender oil, lemon oil, lemongrass, marjoram, *melaleuca*, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, *perilla* oil, pennyroyal oil, peppermint oil, petit grain, pine oil, plum oil, ravensara, red cedar, roman chamomile, rose oil, rosehip oil, rosemary oil, rosewood oil, sandalwood oil, *sassafras* oil, savory oil, schisandra oil, spikenard, spruce, star anise oil, tangerine, tarragon oil, tea tree oil, thyme oil, *tsuga* oil, turmeric, valerian, vetiver oil, western red cedar, wintergreen, yarrow oil, ylang-ylang, and zedoary oil.

Examples of fragrant molecules are alcohols (e.g., furaneol (strawberry), 1-hexanold (herbaceous, woody), cis-3-hexen-1-ol (fresh cut grass), menthol (peppermint), or the like, or a combination comprising at least one of the foregoing alcohols); esters (e.g., fructone (fruity, apple-like), hexyl acetate (apple, floral, fruity), ethyl methyphenylglycidate (strawberry), methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin (extracted from resin of *styrax benzoin* tree); black pepper (from the plant *piper nigrum* of the piperaceae family), cajuput oil (from *melaleuca cajuput*), caraway, carrot seed, coriander, cypress, dill, fennel, helichrysum, lavandin, lemon verena, bee balm (lemon balm essential oil extracted from *Melissa officinalis* of the labiatae family), niaouli, palmarosa, petit grain, *tagetes*, vetiver, or the like, or a combination comprising at least one of the foregoing esters); ketones (e.g., dihydrojasmone (fruity woody floral), oct-1-en-3one (blood, metallic, mushroom-like), 2-acetyl-1-pyrroline (fresh bread, jasmine rice), 6-acetyl-2,3,4,5-tetrahydropyridine (fresh bread, tortillas, popcorn), or the like, or a combination comprising at least one of the foregoing ketones); lactones (γ-decalactone (intense peach flavor), γ-nonalactone (coconut odor, popular in suntan lotions), δ-octalactone (creamy note, jasmine lactone powerful fatty fruity peach and apricot), *massoia* lactone (powerful creamy coconut, wine lactone sweet coconut odor), sotolon (maple syrup, curry, fenugreek), or the like, or a combination comprising at least one of the foregoing lactones); thiols (ethenethiol (commonly called ethyl mercaptan), grapefruit mercaptan (grapefruit), methanethiol (commonly called methyl mercaptan), 2-methyl-2-propanethiol (commonly called tertiary-butyl mercaptan)); linear terpenes (e.g., myrcene (woody, complex), geraniol (rose, flowery), nerol (sweet rose, flowery), citral, lemonal, geranial, neral (lemon, lemon myrtle, lemongrass), citronellal (lemon, lemongrass), citronellol (lemon, lemongrass, rose, *pelargonium*), linalool (floral, sweet, woody, lavender), nerolidol (woody, fresh bark), or the like, or a combination comprising at least one of the foregoing linear terpenes; cyclic terpenes (e.g., limonene, camphor, terpineol, ionone, thujuon, or the like, or a combination comprising at least one of the foregoing cyclic terpenes); aromatic species (e.g., benzaldehyde, eugenol, cinnamaldehyde, ethyl maltol, vanillin, anisole, anethole, estragole, thymol, or the like or a combination comprising at least one of the foregoing aromatic species); amines (e.g., thiethylamine, triethylamine, cadaverine, pyridine, indole, skatole, or the like, or a combination comprising at least one of the foregoing amines) or the like, or a combination comprising at least one of the foregoing fragrant molecules.

Solubilizers are generally used to incorporate oil based ingredient into a water based product. Ingredients like polysorbate 20, polysorbate 80, Caprol Micro Express, Cromollient SCE, and caprylyl/capryl glucoside would be considered solubilizers.

Caprylyl/capryl glucoside (aka octyl/decyl glucoside or C8-10 alkyl polyglucoside) is an Ecocert non-ionic solubilizer with a pH of 5.5 to 6 that can be used as a solubilizer and a very gentle surfactant. It comes to us as a 60% active ingredient product, and the suggested usage is 1% to 10%. It can be used in our surfactant based products to increase viscosity and boost foaming, which is always a bonus, and it can also be used as a very gentle surfactant in things like make-up removers.

Decyl glucoside is produced by the reaction of glucose from corn starch with the fatty alcohol decanol which is derived from coconut(s). It is considered to be biodegradable and created from a renewable resource.

A preservative is a naturally occurring or synthetically produced substance that is added to products such as foods, pharmaceuticals, paints, biological samples, wood, etc. to prevent decomposition by microbial growth or by undesirable chemical changes. Preservatives can be divided into two types, depending on their origin. Class I preservatives refers to those preservatives which are naturally occurring, everyday substances. Examples include sugar, honey, alcohol, salt, and glycerine.

A preservative based on an antimicrobial peptide derived from the lactic acid bacteria, *Leuconostoc kimchii*. *L. kimchii* restricts the growth of other microorganisms by acidifying its environment, and produces a novel antimicrobial peptide as a second mechanism of defense.

Food grade preservatives, like sorbic acid, were also first discovered as a component of a plant. In this case, sorbic acid was discovered in the berries of the rowan tree, *Sorbus aucuparia*, in 1859. The antimicrobial effect of sorbic acid was discovered in the late 1930s. Salts of sorbic acid are the preferred form, as they are water soluble. Potassium sorbate is a commonly used salt of sorbic acid.

It is further contemplated that the present invention may alternatively include natural plant-based fungicides, bactericides, disinfectants, germicides, antiseptics, antibiotics and/or antimicrobials.

Examples of plant materials known to have naturally occurring fungicidal properties include, but are not limited to, *Ajuga bracteosa* Wall. ex Benth., *Aleurites moluccans*, *Allium sativum*, *Aloe barbadensis*, *Aloe vera*, *Anacardium occidentale*, *Anthemis nobilis*, *Arctium lappa*, *Argemone mexicana*, *Artemisia tridentata* Nutt, *Arthraxon hispidus* (Thunb.) Merr., *Arthraxon ciliaris* Beauv., *Arthraxon hispidus* (Thunb.) Merr., *Azadirachta indica*, *Barringtonia racemosa* (L.) Blume ex DC., *Bonafousia muelleriana* (Mart.) Boit. & L. Allorge, *Bonafousia undulata* (Pahl) A.DC., *Calendula officinalis*, *Canarium luzonicum*, *Carica papaya*, *Caryocar villosum* (Aublet) Pers., *Cassia alata*, *Cassia absus*, *Cassia occidentalis*, *Cassia tora*, *Cassuvium pomiferum*, *Celastrus angulatus* Maxim. (*C. latifoliu* Hemsl.)., *Cetraria islandica*, *Chelidonium majus*, *Chlorophora excelsa*, *Citrus sinensis*, *Citrus racemosa*, *Citrus decumana*, *Citrus bigaradia*, *Citrus paradisi*, *Commiphora molmol*, *Commiphora myrrha*, *Coriandrum sativum*, *Cumin cyminum*, *Curcuma amada*, *Cymbopogon citratus* (syn. *Adropogon citratus*), *Echinacea angustifolia*, *Eucalyptus globulus*, *Ficus racemosa*, *Geranium maculatum*, *Hirtella racemosa* Lam., *Iryanthera juruensis* Warb., *Jatropha multifida* Linné, *Jatropha curcas* Linné, *Juglans regia*, *Lavandula officinalis*, *Lavandula angustifolia*, *Lawsonia alba*, *Ligusticum sinense*, *Lygodium circinnatum* (N. L. Burm.) Swartz, *Majorana hortensis*, *Majorana onites*, *Matricaria officinalis*, *Melaleuca alternifolia*, *Origanum majorana*, *Origanum onites*, *Origanum vulgare*, *Origanum heracleoticum*, *Phytolacca decandra*, *Phytolacca americana*, *Phytolacca rigida*, *Pinus silvestris*, *Poria cocas*, *Prostanthera striatiflora*, *Rubus fruticosus*, *Salix babylonica* L., *Scutellaria baiacalensis*, *Thymus vulgaris*, *Trifolium pratense*, *Usnea barbata*, and *Zanha africana*, *Zingiber officinale*.

Examples of plant materials known to have naturally occurring bactericidal properties include, but are not limited to, *Abelmoschus moschatus* Medic., *Allium odorum*, *Allium sativum*, *Aloe barbadensis*, *Aloysia triphylla*, *Anthemis nobilis*, *Artemisia absinthium*, *Bellis perennis*, *Berberis vulgaris*, *Calendula officinalis*, *Canarium luzonicum*, *Caryophyllus aromaticus*, *Centella asiatica*, *Cetraria islandica*, *Cinnamonium zeylanicum*, *Citrus paradisi*, *Citrus limonum*, *Citrus medica*, *Citrus racemosa*, *Citrus decumana*, *Eucalyptus globulus*, *Eugenia caryophyllata*, *Eugenia aromatica*, *Eupatorium fortunei*, *Gentiana lutea*, *Ginkgo biloba*, *Hibiscus abelmoschus*, *Hippophae rhamnoides*, *Humulus lupulus*, *Hydrocotyle asiatica*, *Inula helenium*, *Jambosa caryophyllus*, *Lippia citriodora*, *Lithospermum erythrorhizon*, *Matricaria officinalis*, *Mauritia flexosa*, *Melaleuca alternifolia*, *Monotropa un flora*, *Myrica cerifera*, *Persea americana*, *Phellodendron amurence*, *Propolis*, *Prostanthera striatiflora*, *Salvia officinalis*, *Syzygium aromaticum*, *Taraktogenos kurzii* King, *Thymus vulgaris*, *Usnea barbata*, *Valeriana officinalis*, and *Verbascum Thapsus*.

Examples of plant materials known to have naturally occurring disinfectant properties include, but are not limited to, *Agave americana*, *Allium sativum*, *Allium cepa*, *Aloe barbadensis*, *Aloe vera*, *Arctostaphylos uva-ursi*, *Artemisia abrotanum*, *Artemisia tridentata* Nutt, *Ascophylum nodosum*, *Aster tataricus* L., *Aster tataricus* L., *Baphia nitida*, *Betula pendula*, *Betula alba*, *Calendula officinalis*, *Calluna vulgaris*, *Carum carvi*, *Caryophyllus aromaticus*, *Chrysanthemum parthenium*, *Cinchona succirubra*, *Citrus decumana*, *Citrus paradisi*, *Citrus racemosa*, *Cochlearia officinalis*, *Commiphora myrrha*, *Commiphora molmol*, *Cupresses sempervirens*, *Eucalyptus globulus*, *Eugenia caryophyllata*, *Eugenia aromatica*, *Fagara capensis*, *Humulus lupulus*, *Hydrastis canadensis*, *Hypericum perforatum*, *Jambosa caryophyllus*, *Juglans regia*, *Juniperus communis*, *Kigelia africana*, *Lavandula officinalis*, *Lavandula angustifolia*, *Lygodium circinnatum* (N. L. Burm) Swartz, *Magnolia glauca*, *Majorana hortensis*, *Majorana onites*, *Melaleuca alternifolia*, *Melissa officinalis*, *Mentha piperita*, *Origanum heracleoticum*, *Origanum vulgare*, *Origanum onites*, *Origanum majorana*, *Oxycoccus quadripetalus*, *Petasites vulgaris*, *Pyrola minor*, *Salix vitellina*, *Salvia officinalis*, *Santalum album*, *Saponaria officinalis*, *Solidago virgaurea*, *Symphytum officinale*, *Syzygium aromaticum*, *Tabernaemontana crassa*, *Tanacetum vulgare*, *Tanacetum parthenium*, *Taraktogenos kurzii* King, *Taraxacum officinale*, *Thymus vulgaris*, *Tropaeolum majus*, *Tussilago petasites*, *Umbellularia californica* [H. & A] Nutt., *Vaccinium vitis-idaea*, and *Zanthoxylum capense*.

Examples of plant material known to have naturally occurring germicidal properties include, but are not limited to, *Andira araroba*, *Betula alba*, *Betula pendula*, *Carum copticum*, *Carum ajowan*, *Citrus mitis*, *Citrus microcarpa* Bge. (by Tanaka), *Humulus lupulus*, *Lavandula officinalis*, *Lavandula angustifolia*, *Lithospermum erythrorhizon*, *Melaleuca alternifolia*, *Phellodendron amurence*, *Sclerocarya birrea* subsp. *caffra*, *Thymus vulgaris*, *Trachyspermum ammi*, and *Vaccinium myrtillus*.

Examples of plant material known to have naturally occurring antiseptic properties include, but are not limited to, *Abies cilicia*, *Achillea millefolium*, *Adropogon citratus*, *Agathosma betulina*, *Agave americana*, *Ajuga* spp, *Alkanna tinctoria*, *Alliaria petiolata*, *Allium sativum*, *Allium cepa*, *Aloe barbadensis*, *Amyris balsamifera*, *Anthemis nobilis*, *Anthriscus sylvestris*, *Anthriscus cerefolium*, *Anthyllis vulneraria*, *Apium graveolens*, *Aquilegia vulgaris*, *Arbutus unedo*, *Arctium lappa*, *Arctostaphylos uva-ursi*, *Armeria maritima*, *Armoracia rusticana*, *Arnica montana*, *Artemisia tridentata* Nutt, *Artemisia absinthium*, *Artemisia dracunculus*, *Azadirachta indica*, *Baptisia tinctoria*, *Berberis vulgaris*, *Betula pendula*, *Betula alba*, *Boldea fragrans*, *Boldo boldus*, *Boswellia thurifera*, *Brucea javanica*, *Calendula officinalis*,

*Calluna vulgaris, Cananga odorata, Cannabis sativa, Capsella bursa-pastoris, Capsicum frutescens, capsicum minimum, Carlina acaulis, Carum copticum, Carum ajowan, Carum carvi, Caryophyllus aromaticus, Centaurium erythraea, Centaurium vulgare, Centella asiatica, Cetraria islandica, Chelidonium majus, Chlorophora excelsa, Cinchona succirubra, Cinnamomum cassia, Cinnamomum camphora, Cinnamonium zeylanicum, Citrus bigaradia, Citrus microcarpa* Bge. (by Tanaka), *Citrus mitis, Citrus bergamia, Citrus sinensis, Citrus limonum, Citrus medica, Cnicus benedictus, Commiphora myrrha, Commiphora molmol, Copaifera officinalis, Copaifera multijuga, Copaifera guyanensis, Copaifera reticulata, Corydalis cava, Corydalis ambigua* Cham. et Schlect., *Crithmum maritimum, Cupresses sempervirens, Curcuma amada, Curcuma amada, Cymbopogon citratus, Daucus carota, Diospyros mespiliformis, Echinacea angustifolia, Elettaria cardamomum, Elymus repens, Epigaea repens, Erythraea centaurium, Eucalyptus globulus, Eucryphia lucida, Eugenia caryophyllata, Eugenia aromatica, Eupatorium perfoliatum, Fagus sylvatica, Filipendula ulmaria, Foeniculum vulgare, Fragaria vesca, Galium verum, Gaultheria procumbens, Gentiana lutea, Geranium maculatum, Gerardia pedicularis, Geum urbanum, Gleditschia triacanthos, Gnaphalium stoeches, Gnaphalium citrinum, Gnaphalium dioicum, Gnaphalium polycephalum, Gnaphalium arenarium, Gratiola officinalis, Hamamelis virginiana, Hedeome pulegioides, Hedera helix, Heliotropium europaeum, Hieracium pilosella, Houttuynia cordata, Houyttuyniae cordata, Humulus lupulus, Hydrastis canadensis, Hydrocotyle asiatica, Hypericum perforatum, Hyssopus officinalis, Indigofera tinctoria, Inula heknium, Isatis tinctoria, Jambosa caryophyllus, Juglans regia, Juniperus communis, Lactuca sativa, Lantana camara* Linné, *Larrea divaricata* (DC) Cov., *Lavandula angustifolia, Lavandula officinalis, Legusticum levisticum, Levisticum officinale, Lilium candidum, Liquidambar styraciflua, Lonicera caprifolium, Lonicera periclymenum, Lysimachia nummularia, Magnolia glauca, Matricaria officinalis, Melaleuca leucadendron, Melaleuca alternifolia, Melaleuca viridiflora, Melissa officinalis, Mentha piperita, Meum athamanticum, Mimosa tenuiflora, Musa sapientum, Musa paradisiaca, Myroxylon pereirae, Myroxylon balsamum, Myrtus communis, Nabalus serpentaria, Nymphaea alba major aquatica, Nymphaea candida, Nymphaea lotus, Ocimum basilicum, Paeonia officinalis, Pelargonium odorantissimum, Pelargonium graveolens, Pentaglottis sempervirens, Perilla frutescens, Peumus boldus, Phaulopsis barteri, Phellodendron amurense* Rupr., *Phellodendron amurense, Pilosella officinarum, Pimenta dioica, Pimenta officinalis, Pimpinella anisum, Pinus montana* Mill., *Pinus pumilio* Haenke, *Pinus silvestris, Pinus mughus* Scop., *Pinus mugo* Turra, *Piper methysticum, Plantago major, Plantago lanceolata, Podalyria tinctoria, Pogostemon patchouli* Pellet, *Populus tremula, Prunella vulgaris, Psidium guajava, Pulmonaria officinalis, Pyrola minor, Quercus robur, Quercus petraea, Rhus glabra, Rhus aromatica, Rhus cotinus (Cotinus coggyria), Ribes rubrum, Rosa gallica, Rosmarinus officinalis, Rubia tinctorum, Rubia peregrina, Rubus fruticosus, Rubus fructicosus, Rumex acetosa, Sabbatia angularis, Salix vitellina, Salvia sclarea, Salvia rnultiorrhiza, Salvia officinalis, Sambucus nigra, Sanguinaria canadensis, Santalum album, Sassafras albidum, Satureia hortensis*—Summer Savory, *Satureia montana*—Winter Savory, *Saussurea lappa* Clarke, *Scabiosa arvensis, Scutellaria baiacalensis, Senecio vulgaris, Senecio jacobaea, Serenoa repens, Smilax regelii, Smilax ornata, Solidago virgaurea, Sophora tinctoria, Sphagnum cymbifolium, Spiraea ulmaria, Stachys palustris, Statice caroliniana (limonium), Styrax benzoin, Styrax officinalis, Syzygium aromaticum, Tamarindus indica, Tamariscus narbonensis, Tamarix gallica, Terminalia avicennioides, Terminalia glaucescens, Terminalia ivorensis, Terminalia macroptera, Teucrium chamaedrys, Teucrium scordium, Thymus vulgaris, Tilea europaea, Trachyspermum ammi, Trifolium pratense, Trillium grandiflorum, Trillium erectum, Trillium flavum, Trillium pendulum, Turnera diffusa, Tussilago farfara, Vaccinium vitis-idaea, Vaccinium myrtillus, Verbena officinalis, Viola odorata, Viola canina, Xylopia aethiopica, Zanthoxylum armatum* DC., *Zanthoxylum armatum* DC., and *Zea mays*.

Examples of plant material known to have naturally occurring antibiotic properties include, but are not limited to, *Abies cilicia, Achillea millefolium, Acorus calamus, Agrimonia eupatoria, Agropyrun repens, Alkanna tinctoria, Allium sativum, Allium cepa, Aloe barbadensis, Aloysia triphylla, Ananas sativus, Ananas comosus, Arbutus unedo, Arctium lappa, Armeria maritima, Armoracia rusticana, Artemisia tridentata* Nutt, *Calophyllum inophyllum, Carlina acaulis, Cassia tora, Cassia alata, Cassia occidentalis, Cassia nigricans* Vahl ex D.C., *Cassia absus, Centella asiatica, Cera alba, Cetraria islandica, Cetraria islandica, Citrus sinensis, Citrus bigaradia, Cnicus benedictus, Commiphora molmol, Commiphora myrrha, Curcuma amada, Drosera anglica, Echinacea angustifolia, Elymus repens, Evernia purpuracea, Ginkgo biloba, Gramen caninum vulgatius, Hepatica americana, Hieracium pilosella, Humulus lupulus, Hydrastis canadensis, Hydrocotyle asiatica, Hypericum perforatum, Lepidium sativum, Lippia citriodora, Lupinus sativus, Lycopersicon esculenturn, Lythrum salicaria, Mangifera indica, Melilotus officinalis, Mimosa tenuiflora, Musa sapientum, Musa paradisiaca, Nigella sativa, Pentaglottis sempervirens, Pilosella officinarum, Pinus silvestris, Plumbago zeylanica, Plumbago europaea, Polytrichum* spp, *Prunella vulgaris, Raphanus sativus, Salix vitellina, Santalum album, Solanum esculentum, Solanum lycopersicum, Terminalia avicennioides, Terminalia ivorensis, Terminalia glaucescens, Terminalia macroptera, Trichodesma zeylanicum, Triticum repens, Tropaeolum majus, Usnea barbarta, Viola odorata*, and *Viola canina*.

Examples of plant material known to have naturally occurring antimicrobial properties include, but are not limited to, *Adropogon citratus, Alkanna tinctoria, Allium sativum, Aloe barbadensis, Aniba rosaeodora* Ducke, *Anthemis nobilis, Arctium lappa, Arctostaphylos uva-ursi, Argemone mexicana, Arnica montana, Artemisia tridentata* Nutt, *Azadirachta indica, Baptisia tinctoria, Betula alba, Betula pendula, Calamintha officinalis, Calluna vulgaris, Carum carni, Carum petroselinum, Cassia nigricans* Vahl ex D.C., *Cassia alata, Cassia absus, Cassia occidentalis, Cassia tora, Caulophyllum thalictroides* (L) Michx., *Cetraria islandica, Cimicifuga racemosa, Cinnamomum cassia, Cinnamonium zeylanicum, Cistus villosus, Citrus racemosa, Citrus medica, Citrus limonum, Citrus decumana, Citrus paradisi, Commiphora myrrha, Commiphora molmol, Croton* spp., *Cryptolepis obtusa* N. E. Brown, *Cryptolepis sanguinolenta* Schltr., *Cumin cyminum, Cymbopogon citratus, Daucus carota, Echinacea angustifolia, Eucalyptus globulus, Glycyrrhiza glabra, Gnaphalium stoeches, Gnaphalium polycephalum, Gnaphalium citrinum, Gnaphalium dioicum, Gnaphalium arenarium, Guiera senegalensis, Houyttuyniae cordata, Humulus lupulus, Hydrastis canadensis, Indigofera tinctoria, Juglans regia, Juniperus communis, Lapacho morado, Lapacho colorado, Larrea tridenta, Larrea divaricata* (DC) Cov., *Lavandula officinalis, Lavandula angustifolia, Legusticum levisticum, Levisticum officinale, Lippia chevalieri*

Moldenke, *Matricaria officinalis, Melaleuca alternifolia, Melissa officinalis, Mimosa tenuiflora, Nymphaea alba major aquatica, Nymphaea candida, Ocimum sanctum, Ocimum basilicum, Passiflora incarnata, Pavetta oblongifolia* (Hiern) Bremek, *Pelargonium odorantissimum, Pelargonium graveolens, Pentaglottis sempervirens, Petroselinum crispum, Piliostigma thonningii, Pinus silvestris, Piper methysticum, Plantago major, Plumbago zeylanica, Podalyria tinctoria, Rosmarinus officinalis, Salvia hispanica, Salvia officinalis, Sanguinaria canadensis, Sanguisorba officinalis, Satureia montana, Satureia hortensis, Sophora tinctoria, Terminalia macroptera, Terminalia glaucescens, Terminalia ivorensis, Terminalia avicennioides, Teucrium scorodonia, Teucrium chamaedrys, Thymus vulgaris, Verbena officinalis*.

In general, the present invention is a 100% natural air freshener, comprising:
 water;
 vegetable glycerin;
 a plant-based solubilizer;
 at least one plant essential oil;
 at least one natural preservative; and
 at least one vitamin.

EXAMPLES

Formulation One

| Ingredient | % | Category |
| --- | --- | --- |
| Vitamin K | 0.52% | Ingredient |
| Capryl Glucoside | 1.05 | Ingredient |
| Potassium sorbate | 1.05 | Preservative |
| Leucidal | 1.98 | Preservative |
| Glycerin (vegetable) | 2.1 | Ingredient |
| Berry Essential Oil | 2.31 | Fragrance |
| Water | 90.99 | Ingredient |

Formulation Two

| Ingredient | % | Category |
| --- | --- | --- |
| Vitamin B6 | 0.53% | Ingredient |
| Capryl Glucoside | 1.06 | Ingredient |
| Potassium sorbate | 1.06 | Preservative |
| Leucidal | 1.06 | Preservative |
| Glycerin (vegetable) | 2.12 | Ingredient |
| Lemongrass Essential Oil | 1.06 | Fragrance |
| Peppermint Essential Oil | 1.06 | Fragrance |
| Water | 92.06 | Ingredient |

Formulation Three

| Ingredient | % | Category |
| --- | --- | --- |
| Vitamin D3 | 0.53% | Ingredient |
| Capryl Glucoside | 1.06 | Ingredient |
| Potassium sorbate | 1.06 | Preservative |
| Leucidal | 1.06 | Preservative |
| Glycerin (vegetable) | 2.12 | Ingredient |
| Vanilla Essential Oil | 2.33 | Fragrance |
| Water | 91.84 | Ingredient |

Formulation Four

| Ingredient | % | Category |
| --- | --- | --- |
| Vitamin C | 0.53% | Ingredient |
| Capryl Glucoside | 1.06 | Ingredient |
| Potassium sorbate | 1.06 | Preservative |
| Leucidal | 1.06 | Preservative |
| Glycerin (vegetable) | 2.12 | Ingredient |
| Cool Citrus Herb EO | 1.59 | Fragrance |
| Water | 91.53 | Ingredient |

In a preferred embodiment, the present invention is a 100% natural air freshener, comprising:
 water;
 vegetable glycerin;
 a plant-based solubilizer;
 at least one plant essential oil;
 at least one natural preservative; and
 at least one vitamin.

In an alternative embodiment, the present invention is a 100% natural air freshener, comprising:
 water;
 vegetable glycerin;
 a plant-based solubilizer, wherein the solubilizer is capryl glucoside;
 at least one essential oil selected from the group consisting of berry, lemongrass, peppermint, vanilla and cool citrus herb;
 at least one natural preservative selected from the group consisting of potassium sorbate and leucidal; and
 at least one vitamin selected from the group consisting of vitamins A, B, B complex, B1, B12, B15, B2, B5, B6, C, D, E and K.

In yet another embodiment, the present invention may be further comprised of a combination of essential oils. In a preferred embodiment the essential oils are selected from the group consisting of berries, allspice, juniper, seeds, almond, anise, celery, *cumin*, nutmeg oil, bark, *cassia*, cinnamon, *sassafras*, wood, camphor, cedar, rosewood, sandalwood, agarwood, rhizome, galangal, ginger, leaves, basil, bay leaf, common sage, *eucalyptus*, lemon grass, *melaleuca*, oregano, patchouli, peppermint, pine, rosemary, spearmint, tea tree, thyme, wintergreen, resin, frankincense, myrrh, flowers, *cannabis*, chamomile, clary sage, clove, scented *geranium*, hops, hyssop, jasmine, lavender, manuka, marjoram, rose, ylang-ylang, peel, bergamot, grapefruit, lemon, lime, orange, tangerine, root, valerian, and mango.

In a further embodiment, the present invention may be further comprised of a plant material with naturally occurring fungicidal properties. In a preferred embodiment, the plant material is chosen from the group consisting of *Ajuga bracteosa* Wall. ex Benth., *Aleurites moluccans, Allium sativum, Aloe barbadensis, Aloe vera, Anacardium occidentale, Anthemis nobilis, Arctium lappa, Argemone mexicana, Artemisia tridentata* Nutt, *Arthraxon hispidus* (Thunb.) Merr., *Arthraxon ciliaris* Beauv., *Arthraxon hispidus* (Thunb.) Merr., *Azadirachta indica, Barringtonia racemosa* (L.) Blume ex DC., *Bonafousia muelleriana* (Mart.) Boit. & L. Allorge, *Bonafousia undulata* (Vahl) A.DC., *Calendula officinalis, Canarium luzonicum, Carica papaya, Caryocar villosum* (Aublet) Pers., *Cassia alata, Cassia absus, Cassia occidentalis, Cassia tora, Cassuvium pomiferum, Celastrus angulatus* Maxim. (*C. latifoliu* Hemsl.), *Cetraria islandica, Chelidonium majus, Chlorophora excelsa, Citrus sinensis, Citrus racemosa, Citrus decumana, Citrus bigaradia, Citrus*

*paradisi, Commiphora molmol, Commiphora myrrha, Coriandrum sativum, Cumin cyminum, Curcuma amada, Cymbopogon citratus* (syn. *Adropogon citratus*), *Echinacea angustifblia, Eucalyptus globulus, Ficus racemosa, Geranium maculatum, Hirtella racemosa* Lam., *Iryanthera juruensis* Warb., *Jatropha multifida* Linné, *Jatropha curcas* Linné, *Juglans regia, Lavandula officinalis, Lavandula angustifolia, Lawsonia alba, Ligusticum sinense, Lygodium circinnatum* (N. L. Burm.) Swartz, *Majorana hortensis, Majorana onites, Matricaria officinalis, Melaleuca alternifolia, Origanum majorana, Origanum onites, Origanum vulgare, Origanum heracleoticum, Phytolacca decandra, Phytolacca americana, Phytolacca rigida, Pinus silvestris, Poria cocos, Prostanthera striatiflora, Rubus fruticosus, Salix babylonica* L., *Scutellaria baiacalensis, Thymus vulgaris, Trifolium pratense, Usnea barbata, Zanha africana,* and *Zingiber officinale.*

In a further embodiment, the present invention may be further comprised of a plant material with naturally occurring bactericidal properties. In a preferred embodiment, the plant material is chosen from the group consisting of *Abelmoschus moschatus* Medic., *Allium odorum, Allium sativum, Aloe barbadensis, Aloysia triphylla, Anthemis nobilis, Artemisia absinthium, Bellis perennis, Berberis vulgaris, Calendula officinalis, Canarium luzonicum, Caryophyllus aromaticus, Centella asiatica, Cetraria islandica, Cinnamonium zeylanicum, Citrus paradisi, Citrus limonum, Citrus medica, Citrus racemosa, Citrus decumana, Eucalyptus globulus, Eugenia caryophyllata, Eugenia aromatica, Eupatorium fortunei, Gentiana lutea, Ginkgo biloba, Hibiscus abelmoschus, Hippophae rhamnoides, Humulus lupulus, Hydrocotyle asiatica, Inula helenium, Jambosa caryophyllus, Lippia citriodora, Lithospermum erythrorhizon, Matricaria officinalis, Mauritia flexosa, Melaleuca alternifolia, Monotropa uniflora, Myrica cerifera, Persea americana, Phellodendron amurence, Propolis, Prostanthera striatiflora, Salvia officinalis, Syzygium aromaticum, Taraktogenos kurzii* King, *Thymus vulgaris, Usnea barbata, Valeriana officinalis,* and *Verbascum Thapsus.*

In a further embodiment, the present invention may be further comprised of a plant material with naturally occurring disinfectant properties. In a preferred embodiment, the plant material is chosen from the group consisting of *Agave americana, Allium sativum, Allium cepa, Aloe barbadensis, Aloe vera, Arctostaphylos uva-ursi, Artemisia abrotanum, Artemisia tridentata* Nutt, *Ascophylum nodosum, Aster tataricus* L., *Aster tataricus* L., *Baphia nitida, Betula pendula, Betula alba, Calendula officinalis, Calluna vulgaris, Carum carvi, Caryophyllus aromaticus, Chrysanthemum parthenium, Cinchona succirubra, Citrus decumana, Citrus paradisi, Citrus racemosa, Cochlearia officinalis, Commiphora myrrha, Commiphora molmol, Cupresses sempervirens, Eucalyptus globulus, Eugenia caryophyllata, Eugenia aromatica, Fagara capensis, Humulus lupulus, Hydrastis canadensis, Hypericum perforatum, Jambosa caryophyllus, Juglans regia, Juniperus communis, Kigelia africana, Lavandula officinalis, Lavandula angustifolia, Lygodium circinnatum* (N. L. Burm) Swartz, *Magnolia glauca, Majorana hortensis, Majorana onites, Melaleuca alternifolia, Melissa officinalis, Mentha piperita, Origanum heracleoticum, Origanum vulgare, Origanum onites, Origanum majorana, Oxycoccus quadripetalus, Petasites vulgaris, Pyrola minor, Salix vitellina, Salvia officinalis, Santalum album, Saponaria officinalis, Solidago virgaurea, Symphytum officinale, Syzygium aromaticum, Tabernaemontana crassa, Tanacetum vulgare, Tanacetum parthenium, Taraktogenos kurzii* King, *Taraxacum officinale, Thymus vulgaris, Tropaeolum majus, Tussilago petasites, Umbellularia californica* [H. & A] Nutt., *Vaccinium vitis-idaea,* and *Zanthoxylum capense.*

In a further embodiment, the present invention may be further comprised of a plant material with naturally occurring germicidal properties. In a preferred embodiment, the plant material is chosen from the group consisting of *Andira araroba, Betula alba, Betula pendula, Carum copticum, Carum ajowan, Citrus mitis, Citrus microcarpa* Bge. (by Tanaka), *Humulus lupulus, Lavandula officinalis, Lavandula angustifolia, Lithospermum erythrorhizon, Melaleuca alternifolia, Phellodendron amurence, Sclerocarya birrea* subsp. *caffra, Thymus vulgaris, Trachyspermum ammi,* and *Vaccinium myrtillus.*

In a further embodiment, the present invention may be further comprised of a plant material with naturally occurring antiseptic properties. In a preferred embodiment, the plant material is chosen from the group consisting of *Abies cilicia, Achillea millefolium, Adropogon citratus, Agathosma betulina, Agave americana, Ajuga* spp, *Alkanna tinctoria, Alliaria petiolata, Allium sativum, Allium cepa, Aloe barbadensis, Amyris balsamifera, Anthemis nobilis, Anthriscus sylvestris, Anthriscus cerefolium, Anthyllis vulneraria, Apium graveolens, Aquilegia vulgaris, Arbutus unedo, Arctium lappa, Arctostaphylos uva-ursi, Armeria maritima, Armoracia rusticana, Arnica montana, Artemisia tridentata* Nutt, *Artemisia absinthium, Artemisia dracunculus, Azadirachta indica, Baptisia tinctoria, Berberis vulgaris, Betula pendula, Betula alba, Boldea fragrans, Boldo boldus, Boswellia thurifera, Brucea javanica, Calendula officinalis, Calluna vulgaris, Cananga odorata, Cannabis sativa, Capsella bursa-pastoris, Capsicum frutescens, capsicum minimum, Carlina acaulis, Carum copticum, Carum ajowan, Carum carvi, Caryophyllus aromaticus, Centaurium erythraea, Centaurium vulgare, Centella asiatica, Cetraria islandica, Chelidonium majus, Chlorophora excelsa, Cinchona succirubra, Cinnamomum cassia, Cinnamomum camphora, Cinnamonium zeylanicum, Citrus bigaradia, Citrus microcarpa* Bge. (by Tanaka), *Citrus mitis, Citrus bergamia, Citrus sinensis, Citrus limonum, Citrus medica, Cnicus benedictus, Commiphora myrrha, Commiphora molmol, Copaifera officinalis, Copaifera multijuga, Copaifera guyanensis, Copaifera reticulata, Corydalis cava, Corydalis ambigua* Cham. et Schlect., *Crithmum maritimum, Cupresses sempervirens, Curcuma amada, Curcuma amada, Cymbopogon citratus, Daucus carota, Diospyros mespiliformis, Echinacea angustifolia, Elettaria cardamomum, Elymus repens, Epigaea repens, Erythraea centaurium, Eucalyptus globulus, Eucryphia lucida, Eugenia caryophyllata, Eugenia aromatica, Eupatorium perfoliatum, Fagus sylvatica, Filipendula ulmaria, Foeniculum vulgare, Fragaria vesca, Galium verum, Gaultheria procumbens, Gentiana lutea, Geranium maculatum, Gerardia pedicularis, Geum urbanum, Gleditschia triacanthos, Gnaphalium stoeches, Gnaphalium citrinum, Gnaphalium dioicum, Gnaphalium polycephalum, Gnaphalium arenarium, Gratiola officinalis, Hamamelis virginiana, Hedeome pulegioides, Hedera helix, Heliotropium europaeum, Hieracium pilosella, Houttuynia cordata, Houyttuyniae cordata, Humulus lupulus, Hydrastis canadensis, Hydrocotyle asiatica, Hypericum perforatum, Hyssopus officinalis, Indigofera tinctoria, Inula helenium, Isatis tinctoria, Jambosa caryophyllus, Juglans regia, Juniperus communis, Lactuca sativa, Lantana camara* Linné, *Larrea divaricata* (DC) Cov., *Lavandula angustifolia, Lavandula officinalis, Legusticum levisticum, Levisticum officinale, Lilium candidum, Liquidambar styraciflua, Lonicera caprifolium, Lonicera periclymenum, Lysimachia nummularia, Magnolia glauca, Matricaria officinalis, Melaleuca leucadendron, Melaleuca alternifolia, Melaleuca viridiflora,*

Melissa officinalis, Mentha piperita, Meum athamanticum, Mimosa tenuiflora, Musa sapientum, Musa paradisiaca, Myroxylon pereirae, Myroxylon balsamum, Myrtus communis, Nabalus serpentaria, Nymphaea alba major aquatica, Nymphaea candida, Nymphaea lotus, Ocimum basilicum, Paeonia officinalis, Pelargonium odorantissimum, Pelargonium graveolens, Pentaglottis sempervirens, Perilla frutescens, Peumus boldus, Phaulopsis barteri, Phellodendron amurense Rupr., Phellodendron amurence, Pilosella officinarum, Pimenta dioica, Pimenta officinalis, Pimpinella anisum, Pinus montana Mill., Pinus pumilio Haenke, Pinus silvestris, Pinus mughus Scop., Pinus muga Turra, Piper methysticum, Plantago major, Plantago lanceolata, Podalyria tinctoria, Pogostemon patchouli Pellet, Populus tremula, Prunella vulgaris, Psidium guajava, Pulmonaria officinalis, Pyrola minor, Quercus robur, Quercus petraea, Rhus glabra, Rhus aromatica, Rhus cotinus (Cotinus coggyria), Ribes rubrum, Rosa gallica, Rosmarinus officinalis, Rubia tinctorum, Rubia peregrina, Rubus fruticosus, Rubus fructicosus, Rumex acetosa, Sabbatia angularis, Salix vitellina, Salvia sclarea, Salvia multiorrhiza, Salvia officinalis, Sambucus nigra, Sanguinaria canadensis, Santalum album, Sassafras albidum, Satureia hortensis—Summer Savory, Satureia montana—Winter Savory, Saussurea lappa Clarke, Scabiosa arvensis, Scutellaria baiacalensis, Senecio vulgaris, Senecio jacobaea, Serenoa repens, Smilax regelii, Smilax ornata, Solidago virgaurea, Sophora tinctoria, Sphagnum cymbifolium, Spiraea ulmaria, Stachys palustris, Statice caroliniana (limonium), Styrax benzoin, Styrax officinalis, Syzygium aromaticum, Tamarindus indica, Tamariscus narbonensis, Tamarix gallica, Terminalia avicennioides, Terminalia glaucescens, Terminalia ivorensis, Terminalia macroptera, Teucrium chamaedrys, Teucrium scordium, Thymus vulgaris, Tilea europaea, Trachyspermum ammi, Trifolium pratense, Trillium grandiflorum, Trillium erectum, Trillium flavum, Trillium pendulum, Turnera diffusa, Tussilago farfara, Vaccinium vitis-idaea, Vaccinium myrtillus, Verbena officinalis, Viola odorata, Viola canina, Xylopia aethiopica, Zanthoxylum armatum DC., Zanthoxylum armatum DC., and Zea mays.

In a further embodiment, the present invention may be further comprised of a plant material with naturally occurring antibiotic properties. In a preferred embodiment, the plant material is chosen from the group consisting of Abies cilicia, Achillea millefolium, Acorus calamus, Agrimonia eupatoria, Agropyrun repens, Alkanna tinctoria, Allium sativum, Allium cepa, Aloe barbadensis, Aloysia triphylla, Ananas sativus, Ananas comosus, Arbutus unedo, Arctium lappa, Armeria maritima, Armoracia rusticana, Artemisia tridentata Nutt, Calophyllum inophyllum, Carlina acaulis, Cassia tora, Cassia alata, Cassia occidentalis, Cassia nigricans Vahl ex D.C., Cassia absus, Centella asiatica, Cera alba, Cetraria islandica, Cetraria islandica, Citrus sinensis, Citrus bigaradia, Cnicus benedictus, Commiphora molmol, Commiphora myrrha, Curcuma amada, Drosera anglica, Echinacea angustifolia, Elymus repens, Evernia purpuracea, Ginkgo biloba, Gramen caninum vulgatius, Hepatica americana, Hieracium pilosella, Humulus lupulus, Hydrastis canadensis, Hydrocotyle asiatica, Hypericum perforatum, Lepidium sativum, Lippia citriodora, Lupinus sativus, Lycopersicon esculentum, Lythrum salicaria, Mangifera indica, Melilotus officinalis, Mimosa tenuiflora, Musa sapientum, Musa paradisiaca, Nigella sativa, Pentaglottis sempervirens, Pilosella officinarum, Pinus silvestris, Plumbago zeylanica, Plumbago europaea, Polytrichum spp, Prunella vulgaris, Raphanus sativus, Salix vitellina, Santalum album, Solanum esculentum, Solanum lycopersicum, Terminalia avicennioides, Terminalia ivorensis, Terminalia glaucescens, Terminalia macroptera, Trichodesma zeylanicum, Triticum repens, Tropaeolum majus, Usnea barbarta, Viola odorata, and Viola canina.

In a further embodiment, the present invention may be further comprised of a plant material with naturally occurring antimicrobial properties. In a preferred embodiment, the plant material is chosen from the group consisting of Adropogon citratus, Alkanna tinctoria, Allium sativum, Aloe barbadensis, Aniba rosaeodora Ducke, Anthemis nobilis, Arctium lappa, Arctostaphylos uva-ursi, Argemone mexicana, Arnica montana, Artemisia tridentata Nutt, Azadirachta indica, Baptisia tinctoria, Betula alba, Betula pendula, Calamintha officinalis, Calluna vulgaris, Carum carvi, Carum petroselinum, Cassia nigricans Vahl ex D.C., Cassia alata, Cassia absus, Cassia occidentalis, Cassia tora, Caulophyllum thalictroides (L) Michx., Cetraria islandica, Cimicifuga racemosa, Cinnamomum cassia, Cinnamonium zeylanicum, Cistus villosus, Citrus racemosa, Citrus medica, Citrus limonum, Citrus decumana, Citrus paradisi, Commiphora myrrha, Commiphora molmol, Croton spp., Cryptolepis obtusa N. E. Brown, Cryptolepis sanguinolenta Schltr., Cumin cyminum, Cymbopogon citratus, Daucus carota, Echinacea angustifolia, Eucalyptus globulus, Glycyrrhiza glabra, Gnaphalium stoeches, Gnaphalium polycephalum, Gnaphalium citrinum, Gnaphalium dioicum, Gnaphalium arenarium, Guiera senegalensis, Houyttuyniae cordata, Humulus lupulus, Hydrastis canadensis, Indigofera tinctoria, Juglans regia, Juniperus communis, Lapacho morado, Lapacho colorado, Larrea tridenta, Larrea divaricata (DC) Cov., Lavandula officinalis, Lavandula angustifolia, Legusticum levisticum, Levisticum officinale, Lippia chevalieri Moldenke, Matricaria officinalis, Melaleuca alternifolia, Melissa officinalis, Mimosa tenuiflora, Nymphaea alba major aquatica, Nymphaea candida, Ocimum sanctum, Ocimum basilicum, Passiflora incarnata, Pavetta oblongifolia (Hiern) Bremek, Pelargonium odorantissimum, Pelargonium graveolens, Pentaglottis sempervirens, Petroselinum crispum, Piliostigma thonningii, Pinus silvestris, Piper methysticum, Plantago major, Plumbago zeylanica, Podalyria tinctoria, Rosmarinus officinalis, Salvia hispanica, Salvia officinalis, Sanguinaria canadensis, Sanguisorba officinalis, Satureia montana, Satureia hortensis, Sophora tinctoria, Terminalia macroptera, Terminalia glaucescens, Terminalia ivorensis, Terminalia avicennioides, Teucrium scorodonia, Teucrium chamaedrys, Thymus vulgaris, Verbena officinalis.

Also disclosed is a method of preparing a 100% natural air freshener, wherein the method comprises:
 a) filling a clean vessel with water;
 b) mixing and blending at least a first preservative with the water in step a);
 c) mixing and blending at least a second preservative with the solution of step b);
 d) mixing a vegetable glycerin and at least one vitamin in a separate container;
 e) adding the vitamin mixture with the solution of step b) at high speed;
 f) mixing and blending at least one plant-based solubilizer with the solution of step e) at low speed to avoid foaming; and
 g) mixing and blending at least one plant essential oil with the solution of step f) at low speed to avoid foaming.

In a preferred embodiment, the first preservative is potassium sorbate and the second preservative is luecidal.

In a still further preferred embodiment the at least one vitamin is selected from the group consisting of vitamins A, B, B complex, B1, B12, B15, B2, B5, B6, C, D, E and K.

In yet another embodiment the plant-based solubilizer is capryl glucoside.

In still another embodiment the at least one plant essential oil is selected from the group consisting of berries, allspice, juniper, seeds, almond, anise, celery, *cumin*, nutmeg oil, bark, *cassia*, cinnamon, *sassafras*, wood, camphor, cedar, rosewood, sandalwood, agarwood, rhizome, galangal, ginger, leaves, basil, bay leaf, common sage, *eucalyptus*, lemon grass, *melaleuca*, oregano, patchouli, peppermint, pine, rosemary, spearmint, tea tree, thyme, wintergreen, resin, frankincense, myrrh, flowers, *cannabis*, chamomile, clary sage, clove, scented *geranium*, hops, hyssop, jasmine, lavender, manuka, marjoram, rose, ylang-ylang, peel, bergamot, grapefruit, lemon, lime, orange, tangerine, root, valerian, and mango. In a most preferred embodiment, the at least one plant essential oil is selected from the group consisting of berry, lemongrass, peppermint, vanilla and cool citrus herb.

It will be appreciated that details of the foregoing embodiments, given for purposes of illustration, are not to be construed as limiting the scope of the invention. Although several embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is further defined in the converted utility application and appended claims. Further, it is recognized that many embodiments may be conceived that do not achieve all the advantages of some embodiments, particularly preferred embodiments, yet the absence of a particular advantage shall not be construed to necessarily mean that such an embodiment is outside the scope of the present invention.

The invention claimed is:

1. A method of preparing a formulation of a 100% natural air freshener, wherein the method comprises:
   a) filling a clean vessel with water;
   b) mixing and blending at least a first preservative with the water in step a) to form a solution;
   c) mixing and blending at least a second preservative with the solution of step b);
   d) mixing a vegetable glycerin and at least one vitamin in a separate container to form a vitamin mixture;
   e) adding the vitamin mixture with the solution of step b) at high speed to form a solution;
   f) mixing and blending at least one plant-based solubilizer with the solution of step e) at low speed to avoid foaming to form a solution, wherein the at least one plant-based solubilizer comprises capryl glucoside; and
   g) mixing and blending at least one plant essential oil with the solution of step f) at low speed to avoid foaming to form a solution.

2. The method of claim 1, wherein the at least one plant essential oil is selected from the group consisting of berries, allspice, juniper, seeds, almond, anise, celery, *cumin*, nutmeg oil, bark, *cassia*, cinnamon, *sassafras*, wood, camphor, cedar, rosewood, sandalwood, agarwood, rhizome, galangal, ginger, leaves, basil, bay leaf, common sage, *eucalyptus*, lemon grass, *melaleuca*, oregano, patchouli, peppermint, pine, rosemary, spearmint, tea tree, thyme, wintergreen, resin, frankincense, myrrh, flowers, *cannabis*, chamomile, clary sage, clove, scented *geranium*, hops, hyssop, jasmine, lavender, manuka, marjoram, rose, ylang-ylang, peel, bergamot, grapefruit, lemon, lime, orange, cool citrus herb, tangerine, root, valerian, vanilla, and mango.

3. The method of claim 1, wherein the at least one vitamin is selected from the group consisting of vitamins A, B, B complex, B1, B12, B15, B2, B5, B6, C, D, E and K.

4. The method of claim 1, further comprising:
   h) mixing and blending, with the solution of step g) at least one plant material known to have naturally occurring fungicidal, bactericidal, disinfectant, germicidal, antiseptic, antibiotic and/or antimicrobial properties.

5. The method of claim 4, wherein the at least one plant material known to have naturally occurring fungicidal properties is selected from the group consisting of *Ajuga bracteosa* Wall. ex Benth., *Aleurites moluccans, Allium sativum, Aloe barbadensis, Aloe vera, Anacardium occidentale, Anthemis nobilis, Arctium lappa, Argemone mexicana, Artemisia tridentate* Nutt, *Arthraxon hispidus* (Thunb.) Merr., *Arthraxon ciliaris* Beauv., *Arthraxon hispidus* (Thunb.) Merr., *Azadirachta indica, Barringtonia racemosa* (L) Blume ex DC., *Bonafousia muelleriana* (Mart.) Boit. & L. Allorge, *Bonafousia undulata* (Pahl) ADC, *Calendula officinalis, Canarium luzonicum, Carica papaya, Caryocar villosum* (Aublet) Pers., *Cassia alata, Cassia absus, Cassia occidentalis, Cassia tora, Cassuvium pomiferum, Celastrus angulatus* Maxim. (*C. latifoliu* Hemsl.)., *Cetraria islandica, Chelidonium majus, Chlorophora excelsa, Citrus sinensis, Citrus racemosa, Citrus decumana, Citrus bigaradia, Citrus paradisi, Commiphora molmol, Commiphora myrrha, Coriandrum sativum, Cumin cyminum, Curcuma amada, Cymbopogon citratus* (syn. *Adropogon citratus*), *Echinacea angustifolia, Eucalyptus globulus, Ficus racemosa, Geranium maculatum, Hirtella racemosa* Lam., *Iryanthera juruensis* Warb., *Jatropha multifida* Linné, *Jatropha curcas* Linné, *Juglans regia, Lavandula officinalis, Lavandula angustifolia, Lawsonia alba, Ligusticum sinense, Lygodium circinnatum* (N. L. Burm.) Swartz, *Majorana hortensis, Majorana onites, Matricaria officinalis, Melaleuca alternifolia, Origanum majorana, Origanum onites, Origanum vulgare, Origanum heracleoticum, Phytolacca decandra, Phytolacca americana, Phytolacca rigida, Pinus silvestris, Poria cocos, Prostanthera striatiflora, Rubus fruticosus, Salix babylonica* L., *Scutellaria baiacalensis, Thymus vulgaris, Trifolium pratense, Usnea barbata, Zanha africana*, and *Zingiber officinale*.

6. The method of claim 4, wherein the at least one plant material known to have naturally occurring bactericidal properties is selected from the group consisting of *Abelmoschus moschatus* Medic., *Allium odorum, Allium sativum, Aloe barbadensis, Aloysia triphylla, Anthemis nobilis, Artemisia absinthium, Bellis perennis, Berberis vulgaris, Calendula officinalis, Canarium luzonicum, Caryophyllus aromaticus, Centella asiatica, Cetraria islandica, Cinnamonium zeylanicum, Citrus paradisi, Citrus limonum, Citrus medica, Citrus racemosa, Citrus decumana, Eucalyptus globulus, Eugenia caryophyllata, Eugenia aromatica, Eupatorium fortunei, Gentiana lutea, Ginkgo biloba, Hibiscus abelmoschus, Hippophae rhamnoides, Humulus lupulus, Hydrocotyle asiatica, Inula helenium, Jambosa caryophyllus, Lippia citriodora, Lithospermum erythrorhizon, Matricaria officinalis, Mauritia flexosa, Melaleuca alternifolia, Monotropa uniflora, Myrica cerifera, Persea americana, Phellodendron amurence, Propolis, Prostanthera striatiflora, Salvia officinalis, Syzygium aromaticum, Taraktogenos kurzii* King, *Thymus vulgaris, Usnea barbata, Valeriana officinalis*, and *Verbascum Thapsus*.

7. The method of claim 4, wherein the at least one plant material known to have naturally occurring disinfectant properties is selected from the group consisting of *Agave americana, Allium sativum, Album cepa, Aloe barbadensis, Aloe* vera, *Arctostaphylos uva-ursi, Artemisia abrotanum, Artemisia tridentata* Nutt, *Ascophylum nodosum, Aster tataricus* L., *Aster tataricus* L., *Baphia nitida, Betula pendula, Betula alba, Calendula officinalis, Calluna vulgaris, Carum carvi, Caryophyllus aromaticus, Chrysanthemum parthenium, Cinchona succirubra, Citrus decumana, Citrus paradisi, Citrus racemosa, Cochlearia officinalis, Commiphora myrrha, Commiphora molmol, Cupresses sempervirens, Eucalyptus globulus, Eugenia caryophyllata, Eugenia aromatica, Fagara capensis, Humulus lupulus, Hydrastis canadensis, Hypericum perforatum, Jambosa caryophyllus, Juglans regia, Juniperus communis, Kigelia africana, Lavandula officinalis, Lavandula angustifolia, Lygodium circinnatum* (N. L. Burm.) Swartz, *Magnolia glauca, Majorana hortensis, Majorana onites, Melaleuca alternifolia, Melissa officinalis, Mentha piperita, Origanum heracleoticum, Origanum vulgare, Origanum onites, Origanum majorana, Oxycoccus quadripetalus, Petasites vulgaris, Pyrola minor, Salix vitellina, Salvia officinalis, Santalum album, Saponaria officinalis, Solidago virgaurea, Symphytum officinale, Syzygium aromaticum, Tabernaemontana crassa, Tanacetum vulgare, Tanacetum parthenium, Taraktogenos kurzii* King, *Taraxacum officinale, Thymus vulgaris, Tropaeolum majus, Tussilago petasites, Umbellularia californica* [H. & A.] Nutt., *Vaccinium vitis-idaea*, and *Zanthoxylum capense*.

8. The method of claim 4, wherein the at least one plant material known to have naturally occurring germicidal properties is selected from the group consisting of *Andira araroba, Betula alba, Betula pendula, Carum copticum, Carum ajowan, Citrus mitis, Citrus microcarpa* Bge. (by Tanaka), *Humulus lupulus, Lavandula officinalis, Lavandula angustifolia, Lithospermum erythrorhizon, Melaleuca alternifolia, Phellodendron amurence, Sclerocarya birrea* subsp. *caffra, Thymus vulgaris, Trachyspermum ammi*, and *Vaccinium myrtillus*.

9. The method of claim 4, wherein the at least one plant material known to have naturally occurring antiseptic properties is selected from the group consisting of *Abies cilicia, Achillea millefolium, Adropogon citratus, Agathosma betulina, Agave americana, Ajuga* spp, *Alkanna tinctoria, Alliaria petiolata, Allium sativum, Allium cepa, Aloe barbadensis, Amyris balsamifera, Anthemis nobilis, Anthriscus sylvestris, Anthriscus cerefolium, Anthyllis vulneraria, Apium graveolens, Aquilegia vulgaris, Arbutus unedo, Arctium lappa, Arctostaphylos uva-ursi, Armeria maritima, Armoracia rusticana, Arnica montana, Artemisia tridentata* Nutt, *Artemisia absinthium, Artemisia dracunculus, Azadirachta indica, Baptisia tinctoria, Berberis vulgaris, Betula pendula, Betula alba, Boldea fragrans, Boldo boldus, Boswellia thurifera, Brucea javanica, Calendula officinalis, Calluna vulgaris, Cananga odorata, Cannabis sativa, Capsella bursa-pastoris, Capsicum frutescens, capsicum minimum, Carlina acaulis, Carum copticum, Carum ajowan, Carum carvi, Caryophyllus aromaticus, Centaurium erythraea, Centaurium vulgare, Centella asiatica, Cetraria islandica, Chelidonium majus, Chlorophora excelsa, Cinchona succirubra, Cinnamomum cassia, Cinnamomum camphora, Cinnamonium zeylanicum, Citrus bigaradia, Citrus microcarpa* Bge. (by Tanaka), *Citrus mitis, Citrus bergamia, Citrus sinensis, Citrus limonum, Citrus medica, Cnicus benedictus, Commiphora myrrha, Commiphora molmol, Copaifera officinalis, Copaifera multijuga, Copaifera guyanensis, Copaifera reticulata, Corydalis cava, Corydalis ambigua* Cham. et Schlect., *Crithmum maritimum, Cupresses sempervirens, Curcuma amada, Curcuma amada, Cymbopogon citratus, Daucus carota, Diospyros mespiliformis, Echinacea angustifolia, Elettaria cardamomum, Elymus repens, Epigaea repens, Erythraea centaurium, Eucalyptus globulus, Eucryphia lucida, Eugenia caryophyllata, Eugenia aromatica, Eupatorium perfoliatum, Fagus sylvatica, Filipendula ulmaria, Foeniculum vulgare, Fragaria vesca, Galium verum, Gaultheria procumbens, Gentiana lutea, Geranium maculatum, Gerardia pedicularis, Geum urbanum, Gleditschia triacanthos, Gnaphalium stoeches, Gnaphalium citrinum, Gnaphalium dioicum, Gnaphalium polycephalum, Gnaphalium arenarium, Gratiola officinalis, Hamamelis virginiana, Hedeome pulegioides, Hedera helix, Heliotropium europaeum, Hieracium pilosella, Houttuynia cordata, Houyttuyniae cordata, Humulus lupulus, Hydrastis canadensis, Hydrocotyle asiatica, Hypericum perforatum, Hyssopus officinalis, Indigofera tinctoria, Inula helenium, Isatis tinctoria, Jambosa caryophyllus, Juglans regia, Juniperus communis, Lactuca sativa, Lantana camara* Linné, *Larrea divaricata* (DC) Cov., *Lavandula angustifolia, Lavandula officinalis, Legusticum levisticum, Levisticum officinale, Lilium candidum, Liquidambar styraciflua, Lonicera caprifolium, Lonicera periclymenum, Lysimachia nummularia, Magnolia glauca, Matricaria officinalis, Melaleuca leucadendron, Melaleuca alternifolia, Melaleuca viridiflora, Melissa officinalis, Mentha piperita, Meum athamanticum, Mimosa tenuiflora, Musa sapientum, Musa paradisiaca, Myroxylon pereirae, Myroxylon balsamum, Myrtus communis, Nabalus serpentaria, Nymphaea alba major aquatica, Nymphaea candida, Nymphaea lotus, Ocimum basilicum, Paeonia officinalis, Pelargonium odorantissimum, Pelargonium graveolens, Pentaglottis sempervirens, Perilla frutescens, Peumus boldus, Phaulopsis barteri, Phellodendron amurense* Rupr., *Phellodendron amurence, Pilosella officinarum, Pimento dioica, Pimento officinalis, Pimpinella anisum, Pinus montana* Mill., *Pinus pumilio* Haenke, *Pinus silvestris, Pinus mughus* Scop., *Pinus mugo* Turra, *Piper methysticum, Plantago major, Plantago lanceolata, Podalyria tinctoria, Pogostemon patchouli* Pellet, *Populus tremula, Prunella vulgaris, Psidium guajava, Pulmonaria officinalis, Pyrola minor, Quercus robur, Quercus petraea, Rhus glabra, Rhus aromatica, Rhus cotinus* (*Cotinus coggyria*), *Ribes rubrum, Rosa gallica, Rosmarinus officinalis, Rubia tinctorum, Rubia peregrina, Rubus fruticosus, Rubus fructicosus, Rumex acetosa, Sabbatia angularis, Salix vitellina, Salvia sclarea, Salvia multiorrhiza, Salvia officinalis, Sambucus nigra, Sanguinaria canadensis, Santalum album, Sassafras albidum, Satureia hortensis*—Summer Savory, *Satureia montana*—Winter Savory, *Saussurea lappa* Clarke, *Scabiosa arvensis, Scutellaria baiacalensis, Senecio vulgaris, Senecio jacobaea, Serenoa repens, Smilax regelii, Smilax ornata, Solidago virgaurea, Sophora tinctoria, Sphagnum cymbifolium, Spiraea ulmaria, Stachys palustris, Statice caroliniana* (*limonium*), *Styrax benzoin, Styrax officinalis, Syzygium aromaticum, Tamarindus indica, Tamariscus narbonensis, Tamarix gallica, Terminalia avicennioides, Terminalia glaucescens, Terminalia ivorensis, Terminalia macroptera, Teucrium chamaethys, Teucrium scordium, Thymus vulgaris, Tilea europaea, Trachyspermum ammi, Trifolium pratense, Trillium grandiflorum, Trillium erectum, Trillium flavum, Trillium pendulum, Turnera diffusa, Tussilago farfara, Vaccinium vitis-idaea, Vaccinium myrtillus, Verbena officinalis, Viola odorata, Viola canina, Xylopia aethiopica, Zanthoxylum armatum* DC., *Zanthoxylum armatum* DC., and *Zea mays*.

10. The method of claim 4, wherein the at least one plant material known to have naturally occurring antibiotics properties is selected from the group consisting of *Abies cilicia, Achillea millefolium, Acorus calamus, Agrimonia eupatoria, Agropyrun repens, Alkanna tinctoria, Allium* sativum, *Allium cepa, Aloe barbadensis, Aloysia triphylla, Ananas sativus,*

*Ananas comosus, Arbutus unedo, Arctium lappa, Armeria maritima, Armoracia rusticana, Artemisia tridentata* Nutt, *Calophyllum inophyllum, Carlina acaulis, Cassia tora, Cassia alata, Cassia occidentalis, Cassia nigricans* Vahl ex D.C., *Cassia absus, Centella asiatica, Cera alba, Cetraria islandica, Cetraria islandica, Citrus sinensis, Citrus bigaradia, Cnicus benedictus, Commiphora molmol, Commiphora myrrha, Curcuma amada, Drosera anglica, Echinacea angustifolia, Elymus repens, Evernia purpuracea, Ginkgo biloba, Gramen caninum vulgatius, Hepatica americana, Hieracium pilosella, Humulus lupulus, Hydrastis canadensis, Hydrocotyle asiatica, Hypericum perforatum, Lepidium sativum, Lippia citriodora, Lupinus sativus, Lycopersicon esculentum, Lythrum salicaria, Mangifera indica, Melilotus officinalis, Mimosa tenuiflora, Musa sapientum, Musa paradisiaca, Nigella sativa, Pentaglottis sempervirens, Pilosella officinarum, Pinus silvestris, Plumbago zeylanica, Plumbago europaea, Polytrichum* spp, *Prunella vulgaris, Raphanus sativus, Salix vitellina, Santalum album, Solanum esculentum, Solanum lycopersicum, Terminalia avicennioides, Terminalia ivorensis, Terminalia glaucescens, Terminalia macroptera, Trichodesma zeylanicum, Triticum repens, Tropaeolum majus, Usnea barbarta, Viola odorata,* and *Viola canina.*

11. The method of claim 4, wherein the at least one plant material known to have naturally occurring antimicrobial properties is selected from the group consisting of *Adropogon citratus, Alkanna tinctoria, Allium sativum, Aloe barbadensis, Aniba rosaeodora* Ducke, *Anthemis nobilis, Arctium lappa, Arctostaphylos uva-ursi, Argemone mexicana, Arnica montana, Artemisia tridentata* Nutt, *Azadirachta indica, Baptisia tinctoria, Betula alba, Betula pendula, Calamintha officinalis, Calluna vulgaris, Carum carni, Carum petroselinum, Cassia nigricans* Vahl ex D.C., *Cassia alata, Cassia absus, Cassia occidentalis, Cassia tora, Caulophyllum thalictroides* (L) Michx., *Cetraria islandica, Cimicifuga racemosa, Cinnamomum cassia, Cinnamonium zeylanicum, Cistus villosus, Citrus racemosa, Citrus medica, Citrus limonum, Citrus decumana, Citrus paradisi, Commiphora myrrha, Commiphora molmol, Croton* spp., *Cryptolepis obtusa* N. E. Brown, *Cryptolepis sanguinolenta* Schltr., *Cumin cyminum, Cymbopogon citratus, Daucus carota, Echinacea angustifolia, Eucalyptus globulus, Glycyrrhiza glabra, Gnaphalium stoeches, Gnaphalium polycephalum, Gnaphalium citrinum, Gnaphalium dioicum, Gnaphalium arenarium, Guiera senegalensis, Houyttuyniae cordata, Humulus lupulus, Hydrastis canadensis, Indigofera tinctoria, Juglans regia, Juniperus communis, Lapacho morado, Lapacho colorado, Larrea tridenta, Larrea divaricata* (DC) Cov., *Lavandula officinalis, Lavandula angustifolia, Legusticum levisticum, Levisticum officinale, Lippia chevalieri* Moldenke, *Matricaria officinalis, Melaleuca alternifolia, Melissa officinalis, Mimosa tenuiflora, Nymphaea alba major aquatica, Nymphaea candida, Ocimum sanctum, Ocimum basilicum, Passiflora incarnata, Pavetta oblongifolia* (Hiern) Bremek, *Pelargonium odorantissimum, Pelargonium graveolens, Pentaglottis sempervirens, Petroselinum crispum, Piliostigma thonningii, Pinus silvestris, Piper methysticum, Plantago major, Plumbago zeylanica, Podalyria tinctoria, Rosmarinus officinalis, Salvia hispanica, Salvia officinalis, Sanguinaria canadensis, Sanguisorba officinalis, Satureia montana, Satureia hortensis, Sophora tinctoria, Terminalia macroptera, Terminalia glaucescens, Terminalia ivorensis, Terminalia avicennioides, Teucrium scorodonia, Teucrium chamaedrys, Thymus vulgaris,* and *Verbena officinalis.*

12. A method of preparing a formulation of a 100% natural air freshener, wherein the method comprises:

a) filling a clean vessel with water;
b) mixing and blending at least a first preservative with the water in step a) to form a solution, wherein the first preservative is potassium sorbate;
c) mixing and blending at least a second preservative with the solution of step b), wherein the second preservative is leucidal;
d) mixing a vegetable glycerin and at least one vitamin in a separate container to form a vitamin mixture;
e) adding the vitamin mixture with the solution of step b) at high speed to form a solution;
f) mixing and blending at least one plant-based solubilizer with the solution of step e) at low speed to avoid foaming to form a solution, wherein the at least one plant-based solubilizer comprises capryl glucoside; and
g) mixing and blending at least one plant essential oil with the solution of step f) at low speed to avoid foaming to form a solution.

13. The method of claim 12, wherein the at least one plant essential oil is selected from the group consisting of berries, allspice, juniper, seeds, almond, anise, celery, *cumin*, nutmeg oil, bark, *cassia*, cinnamon, *sassafras*, wood, camphor, cedar, rosewood, sandalwood, agarwood, rhizome, galangal, ginger, leaves, basil, bay leaf, common sage, *eucalyptus*, lemon grass, *melaleuca*, oregano, *patchouli*, peppermint, pine, rosemary, spearmint, tea tree, thyme, wintergreen, resin, frankincense, myrrh, flowers, *cannabis*, chamomile, clary sage, clove, scented *geranium*, hops, hyssop, jasmine, lavender, manuka, marjoram, rose, ylang-ylang, peel, bergamot, grapefruit, lemon, lime, orange, cool citrus herb, tangerine, root, valerian, vanilla, and mango.

14. The method of claim 12, wherein the at least one vitamin is selected from the group consisting of vitamins A, B, B complex, B1, B12, B15, B2, B5, B6, C, D, E and K.

15. The method of claim 12, further comprising:

h) mixing and blending, with the solution of step g) at least one plant material known to have naturally occurring fungicidal, bactericidal, disinfectant, germicidal, antiseptic, antibiotic and/or antimicrobial properties.

16. The method of claim 15, wherein the at least one plant material known to have naturally occurring fungicidal properties is selected from the group consisting of *Ajuga bracteosa* Wall. ex Benth., *Aleurites moluccans, Allium sativum, Aloe barbadensis, Aloe vera, Anacardium occidentale, Anthemis nobilis, Arctium lappa, Argemone mexicana, Artemisia tridentate* Nutt, *Arthraxon hispidus* (Thunb.) Merr., *Arthraxon ciliaris* Beauv., *Arthraxon hispidus* (Thunb.) Merr., *Azadirachta indica, Barringtonia racemosa* (L) Blume ex DC., *Bonafousia muelleriana* (Mart.) Boit. & L. Allorge, *Bonafousia undulata* (Pahl) ADC, *Calendula officinalis, Canarium luzonicum, Carica papaya, Caryocar villosum* (Aublet) Pers., *Cassia alata, Cassia absus, Cassia occidentalis, Cassia tora, Cassuvium pomiferum, Celastrus angulatus* Maxim. (C. *latifoliu* Hemsl.)., *Cetraria islandica, Chelidonium majus, Chlorophora excelsa, Citrus sinensis, Citrus racemosa, Citrus decumana, Citrus bigaradia, Citrus paradisi, Commiphora molmol, Commiphora myrrha, Coriandrum sativum, Cumin cyminum, Curcuma amada, Cymbopogon citratus* (syn. *Adropogon citratus*), *Echinacea angustifolia, Eucalyptus globulus, Ficus racemosa, Geranium maculatum, Hirtella racemosa* Lam., *Iryanthera juruensis* Warb., *Jatropha multifida* Linné, *Jatropha curcas* Linné, *Juglans regia, Lavandula officinalis, Lavandula angustifolia, Lawsonia alba, Ligusticum sinense, Lygodium circinnatum* (N. L. Burm.) Swartz, *Majorana hortensis, Majorana onites, Matricaria officinalis, Melaleuca alternifolia, Origanum majorana, Origanum onites, Origanum vul-*

*gare, Origanum heracleoticum, Phytolacca decandra, Phytolacca americana, Phytolacca rigida, Pinus silvestris, Poria cocos, Prostanthera striatiflora, Rubus fruticosus, Salix babylonica* L., *Scutellaria baiacalensis, Thymus vulgaris, Trifolium pratense, Usnea barbata, Zanha africana*, and *Zingiber officinale*.

17. The method of claim 15, wherein the at least one plant material known to have naturally occurring bactericidal properties is selected from the group consisting of *Abelmoschus moschatus* Medic., *Allium odorum, Allium sativum, Aloe barbadensis, Aloysia triphylla, Anthemis nobilis, Artemisia absinthium, Bellis perennis, Berberis vulgaris, Calendula officinalis, Canarium luzonicum, Caryophyllus aromaticus, Centella asiatica, Cetraria islandica, Cinnamonium zeylanicum, Citrus paradisi, Citrus limonum, Citrus medica, Citrus racemosa, Citrus decumana, Eucalyptus globulus, Eugenia caryophyllata, Eugenia aromatica, Eupatorium fortunei, Gentiana lutea, Ginkgo biloba, Hibiscus abelmoschus, Hippophae rhamnoides, Humulus lupulus, Hydrocotyle asiatica, Inula helenium, Jambosa caryophyllus, Lippia citriodora, Lithospermum erythrorhizon, Matricaria officinalis, Mauritia flexosa, Melaleuca alternifolia, Monotropa uniflora, Myrica cerifera, Persea americana, Phellodendron amurence, Propolis, Prostanthera striatiflora, Salvia officinalis, Syzygium aromaticum, Taraktogenos kurzii* King, *Thymus vulgaris, Usnea barbata, Valeriana officinalis*, and *Verbascum Thapsus*.

18. The method of claim 15, wherein the at least one plant material known to have naturally occurring disinfectant properties is selected from the group consisting of *Agave americana, Allium sativum, Album cepa, Aloe barbadensis, Aloe vera, Arctostaphylos uva-ursi, Artemisia abrotanum, Artemisia tridentata* Nutt, *Ascophylum nodosum, Aster tataricus* L., *Aster tataricus* L., *Baphia nitida, Betula pendula, Betula alba, Calendula officinalis, Calluna vulgaris, Carum carvi, Caryophyllus aromaticus, Chrysanthemum parthenium, Cinchona succirubra, Citrus decumana, Citrus paradisi, Citrus racemosa, Cochlearia officinalis, Commiphora myrrha, Commiphora molmol, Cupresses sempervirens, Eucalyptus globulus, Eugenia caryophyllata, Eugenia aromatica, Fagara capensis, Humulus lupulus, Hydrastis canadensis, Hypericum perforatum, Jambosa caryophyllus, Juglans regia, Juniperus communis, Kigelia africana, Lavandula officinalis, Lavandula angustifolia, Lygodium circinnatum* (N. L. Burm.) Swartz, *Magnolia glauca, Majorana hortensis, Majorana onites, Melaleuca alternifolia, Melissa officinalis, Mentha piperita, Origanum heracleoticum, Origanum vulgare, Origanum onites, Origanum majorana, Oxycoccus quadripetalus, Petasites vulgaris, Pyrola minor, Salix vitellina, Salvia officinalis, Santalum album, Saponaria officinalis, Solidago virgaurea, Symphytum officinale, Syzygium aromaticum, Tabernaemontana crassa, Tanacetum vulgare, Tanacetum parthenium, Taraktogenos kurzii* King, *Taraxacum officinale, Thymus vulgaris, Tropaeolum majus, Tussilago petasites, Umbellularia californica* [H. & A.] Nutt., *Vaccinium vitis-idaea*, and *Zanthoxylum capense*.

19. The method of claim 15, wherein the at least one plant material known to have naturally occurring germicidal properties is selected from the group consisting of *Andira araroba, Betula alba, Betula pendula, Carum copticum, Carum ajowan, Citrus mitis, Citrus microcarpa* Bge. (by Tanaka), *Humulus lupulus, Lavandula officinalis, Lavandula angustifolia, Lithospermum erythrorhizon, Melaleuca alternifolia, Phellodendron amurence, Sclerocarya birrea* subsp. *caffra, Thymus vulgaris, Trachyspermum ammi*, and *Vaccinium myrtillus*.

20. The method of claim 15, wherein the at least one plant material known to have naturally occurring antiseptic properties is selected from the group consisting of *Abies cilicia, Achillea millefolium, Adropogon citratus, Agathosma betulina, Agave americana, Ajuga* spp, *Alkanna tinctoria, Alliaria petiolata, Allium sativum, Allium cepa, Aloe barbadensis, Amyris balsamifera, Anthemis nobilis, Anthriscus sylvestris, Anthriscus cerefolium, Anthyllis vulneraria, Apium graveolens, Aquilegia vulgaris, Arbutus unedo, Arctium lappa, Arctostaphylos uva-ursi, Armeria maritima, Armoracia rusticana, Arnica montana, Artemisia tridentata* Nutt, *Artemisia absinthium, Artemisia dracunculus, Azadirachta indica, Baptisia tinctoria, Berberis vulgaris, Betula pendula, Betula alba, Boldea fragrans, Boldo boldus, Boswellia thurifera, Brucea javanica, Calendula officinalis, Calluna vulgaris, Cananga odorata, Cannabis sativa, Capsella bursa-pastoris, Capsicum frutescens, capsicum minimum, Carlina acaulis, Carum copticum, Carum ajowan, Carum carvi, Caryophyllus aromaticus, Centaurium erythraea, Centaurium vulgare, Centella asiatica, Cetraria islandica, Chelidonium majus, Chlorophora excelsa, Cinchona succirubra, Cinnamomum cassia, Cinnamomum camphora, Cinnamonium zeylanicum, Citrus bigaradia, Citrus macrocarpa* Bge. (by Tanaka), *Citrus mitis, Citrus bergamia, Citrus sinensis, Citrus limonum, Citrus medica, Cnicus benedictus, Commiphora myrrha, Commiphora molmol, Copaifera officinalis, Copaifera multijuga, Copaifera guyanensis, Copaifera reticulata, Corydalis cava, Corydalis ambigua* Cham. et Schlect., *Crithmum maritimum, Cupresses sempervirens, Curcuma amada, Curcuma amada, Cymbopogon citratus, Daucus carota, Diospyros mespiliformis, Echinacea angustifolia, Elettaria cardamomum, Elymus repens, Epigaea repens, Erythraea centaurium, Eucalyptus globulus, Eucryphia lucida, Eugenia caryophyllata, Eugenia aromatica, Eupatorium perfoliatum, Fagus sylvatica, Filipendula ulmaria, Foeniculum vulgare, Fragaria vesca, Galium verum, Gaultheria procumbens, Gentiana lutea, Geranium maculatum, Gerardia pedicularis, Geum urbanum, Gleditschia triacanthos, Gnaphalium stoeches, Gnaphalium citrinum, Gnaphalium dioicum, Gnaphalium polycephalum, Gnaphalium arenarium, Gratiola officinalis, Hamamelis virginiana, Hedeome pulegioides, Hedera helix, Heliotropium europaeum, Hieracium pilosella, Houttuynia cordata, Houyttuyniae cordata, Humulus lupulus, Hydrastis canadensis, Hydrocotyle asiatica, Hypericum perforatum, Hyssopus officinalis, Indigofera tinctoria, Inula helenium, Isatis tinctoria, Jambosa caryophyllus, Juglans regia, Juniperus communis, Lactuca sativa, Lantana camara* Linné, *Larrea divaricata* (DC) Cov., *Lavandula angustifolia, Lavandula officinalis, Legusticum levisticum, Levisticum officinale, Lilium candidum, Liquidambar styraciflua, Lonicera caprifolium, Lonicera periclymenum, Lysimachia nummularia, Magnolia glauca, Matricaria officinalis, Melaleuca leucadendron, Melaleuca alternifolia, Melaleuca viridiflora, Melissa officinalis, Mentha piperita, Meum athamanticum, Mimosa tenuiflora, Musa sapientum, Musa paradisiaca, Myroxylon pereirae, Myroxylon balsamum, Myrtus communis, Nabalus serpentaria, Nymphaea alba major aquatica, Nymphaea candida, Nymphaea lotus, Ocimum basilicum, Paeonia officinalis, Pelargonium odorantissimum, Pelargonium graveolens, Pentaglottis sempervirens, Perilla frutescens, Peumus boldus, Phaulopsis barteri, Phellodendron amurense* Rupr., *Phellodendron amurence, Pilosella officinarum, Pimento dioica, Pimento officinalis, Pimpinella anisum, Pinus montana* Mill., *Pinus pumilio* Haenke, *Pinus silvestris, Pinus mughus* Scop., *Pinus mugo* Turra, *Piper methysticum, Plantago major, Plantago lanceolata, Podalyria tinctoria, Pogostemon patchouli* Pellet, *Populus* tremula, *Prunella vulgaris, Psidium guajava, Pulmonaria officinalis, Pyrola minor, Quercus robur, Quercus petraea, Rhus glabra, Rhus aromatica, Rhus cotinus* (*Cotinus coggyria*), *Ribes rubrum, Rosa gallica, Rosmarinus officinalis, Rubia tinctorum, Rubia peregrina, Rubus fruticosus, Rubus fructicosus, Rumex acetosa, Sabbatia angularis, Salix vitellina, Salvia sclarea, Salvia multiorrhiza, Salvia officinalis, Sambucus nigra, Sanguinaria canadensis, Santalum album, Sassafras albidum, Satureia hortensis*—Summer Savory, *Satureia montana*—Winter Savory, *Saussurea lappa* Clarke, *Scabiosa arvensis, Scutellaria baiacalensis, Senecio vulgaris, Senecio jacobaea, Serenoa repens, Smilax regelii, Smilax ornata, Solidago virgaurea, Sophora tinctoria, Sphagnum cymbifolium, Spiraea ulmaria, Stachys palustris, Statice caroliniana* (*limonium*), *Styrax benzoin, Styrax officinalis, Syzygium aromaticum, Tamarindus indica, Tamariscus narbonensis, Tamarix gallica, Terminalia avicennioides, Terminalia glaucescens, Terminalia ivorensis, Terminalia macroptera, Teucrium chamaethys, Teucrium scordium, Thymus vulgaris, Tilea europaea, Trachyspermum ammi, Trifolium pratense, Trillium grandiflorum, Trillium erectum, Trillium flavum, Trillium pendulum, Turnera diffusa, Tussilago farfara, Vaccinium vitis-idaea, Vaccinium myrtillus, Verbena officinalis, Viola odorata, Viola canina, Xylopia aethiopica, Zanthoxylum armatum* DC., *Zanthoxylum armatum* DC., and *Zea mays*.

21. The method of claim 15, wherein the at least one plant material known to have naturally occurring antibiotics properties is selected from the group consisting of *Abies cilicia, Achillea millefolium, Acorus calamus, Agrimonia eupatoria, Agropyrun repens, Alkanna tinctoria, Allium sativum, Allium cepa, Aloe barbadensis, Aloysia triphylla, Ananas sativus, Ananas comosus, Arbutus unedo, Arctium lappa, Armeria maritima, Armoracia rusticana, Artemisia tridentata* Nutt, *Calophyllum inophyllum, Carlina acaulis, Cassia tora, Cassia alata, Cassia occidentalis, Cassia nigricans* Vahl ex D.C., *Cassia absus, Centella asiatica, Cera alba, Cetraria islandica, Cetraria islandica, Citrus sinensis, Citrus bigaradia, Cnicus benedictus, Commiphora molmol, Commiphora myrrha, Curcuma amada, Drosera anglica, Echinacea angustifolia, Elymus repens, Evernia purpuracea, Ginkgo biloba, Gramen caninum vulgatius, Hepatica americana, Hieracium pilosella, Humulus lupulus, Hydrastis canadensis, Hydrocotyle asiatica, Hypericum perforatum, Lepidium sativum, Lippia citriodora, Lupinus sativus, Lycopersicon esculentum, Lythrum salicaria, Mangifera indica, Melilotus officinalis, Mimosa tenuiflora, Musa sapientum, Musa paradisiaca, Nigella sativa, Pentaglottis sempervirens, Pilosella officinarum, Pinus silvestris, Plumbago zeylanica, Plumbago europaea, Polytrichum* spp, *Prunella vulgaris, Raphanus sativus, Salix vitellina, Santalum album, Solanum esculentum, Solanum lycopersicum, Terminalia avicennioides, Terminalia ivorensis, Terminalia glaucescens, Terminalia macroptera, Trichodesma zeylanicum, Triticum repens, Tropaeolum majus, Usnea barbarta, Viola odorata*, and *Viola canina*.

22. The method of claim 15, wherein the at least one plant material known to have naturally occurring antimicrobial properties is selected from the group consisting of *Adropogon citratus, Alkanna tinctoria, Allium sativum, Aloe barbadensis, Aniba rosaeodora* Ducke, *Anthemis nobilis, Arctium lappa, Arctostaphylos uva-ursi, Argemone mexicana, Arnica montana, Artemisia tridentata* Nutt, *Azadirachta indica, Baptisia tinctoria, Betula alba, Betula pendula, Calamintha officinalis, Calluna vulgaris, Carum carni, Carum petroselinum, Cassia nigricans* Vahl ex D.C., *Cassia alata, Cassia absus, Cassia occidentalis, Cassia tora, Caulophyllum thalictroides* (L) Michx., *Cetraria islandica, Cimicifuga racemosa, Cinnamomum cassia, Cinnamonium zeylanicum, Cistus villosus, Citrus racemosa, Citrus medica, Citrus limonum, Citrus decumana, Citrus paradisi, Commiphora myrrha, Commiphora molmol, Croton* spp., *Cryptolepis obtusa* N. E. Brown, *Cryptolepis sanguinolenta* Schltr., *Cumin cyminum, Cymbopogon citratus, Daucus carota, Echinacea angustifolia, Eucalyptus globulus, Glycyrrhiza glabra, Gnaphalium stoeches, Gnaphalium polycephalum, Gnaphalium citrinum, Gnaphalium dioicum, Gnaphalium arenarium, Guiera senegalensis, Houyttuyniae cordata, Humulus lupulus, Hydrastis canadensis, Indigofera tinctoria, Juglans regia, Juniperus communis, Lapacho morado, Lapacho colorado, Larrea tridenta, Larrea divaricata* (DC) Cov., *Lavandula officinalis, Lavandula angustifolia, Legusticum levisticum, Levisticum officinale, Lippia chevalieri* Moldenke, *Matricaria officinalis, Melaleuca alternifolia, Melissa officinalis, Mimosa tenuiflora, Nymphaea alba major aquatica, Nymphaea candida, Ocimum sanctum, Ocimum basilicum, Passiflora incarnata, Pavetta oblongifolia* (Hiern) Bremek, *Pelargonium odorantissimum, Pelargonium graveolens, Pentaglottis sempervirens, Petroselinum crispum, Piliostigma thonningii, Pinus silvestris, Piper methysticum, Plantago major, Plumbago zeylanica, Podalyria tinctoria, Rosmarinus officinalis, Salvia hispanica, Salvia officinalis, Sanguinaria canadensis, Sanguisorba officinalis, Satureia montana, Satureia hortensis, Sophora tinctoria, Terminalia macroptera, Terminalia glaucescens, Terminalia ivorensis, Terminalia avicennioides, Teucrium scorodonia, Teucrium chamaedrys, Thymus vulgaris*, and *Verbena officinalis*.

\* \* \* \* \*